US011998647B2

(12) United States Patent
Paver, Jr.

(10) Patent No.: US 11,998,647 B2
(45) Date of Patent: Jun. 4, 2024

(54) ULTRAVIOLET AND MISTING DISINFECTING UNIT

(71) Applicant: Connelly Family Company LLC, Bloomfield Hills, MI (US)

(72) Inventor: Stephen J. Paver, Jr., Troy, MI (US)

(73) Assignee: Connelly Family Company LLC, Bloomfield Hills, MI (US)

( * ) Notice: Subject to any disclaimer, the term of this patent is extended or adjusted under 35 U.S.C. 154(b) by 607 days.

(21) Appl. No.: 16/922,149

(22) Filed: Jul. 7, 2020

(65) Prior Publication Data

US 2020/0330632 A1 Oct. 22, 2020

Related U.S. Application Data

(60) Division of application No. 15/667,969, filed on Aug. 3, 2017, now Pat. No. 10,729,796, which is a continuation of application No. 15/003,456, filed on Jan. 21, 2016, now Pat. No. 9,750,832.

(60) Provisional application No. 62/164,775, filed on May 21, 2015.

(51) Int. Cl.
| | |
|---|---|
| *A61L 2/10* | (2006.01) |
| *A61L 2/00* | (2006.01) |
| *A61L 2/18* | (2006.01) |
| *A61L 2/20* | (2006.01) |
| *A61L 2/22* | (2006.01) |
| *A61L 2/24* | (2006.01) |

(52) U.S. Cl.
CPC .............. *A61L 2/10* (2013.01); *A61L 2/0088* (2013.01); *A61L 2/18* (2013.01); *A61L 2/208* (2013.01); *A61L 2/22* (2013.01); *A61L 2/24* (2013.01); *A61L 2209/111* (2013.01); *A61L 2209/134* (2013.01); *A61L 2209/135* (2013.01); *A61L 2209/21* (2013.01); *A61L 2209/212* (2013.01)

(58) Field of Classification Search
CPC . A61L 2/10; A61L 2/0088; A61L 2/18; A61L 2/208; A61L 2/22; A61L 2/24; A61L 2209/111; A61L 2209/134; A61L 2209/135; A61L 2209/21; A61L 2209/212
See application file for complete search history.

(56) References Cited

U.S. PATENT DOCUMENTS

| | | | |
|---|---|---|---|
| 2,473,174 A | 6/1949 | Pifer | |
| 4,492,477 A * | 1/1985 | Leser | G01N 21/958 356/239.8 |
| 7,790,477 B2 | 9/2010 | Liang et al. | |
| 9,107,973 B1 * | 8/2015 | Robinson | A61L 2/10 |
| 9,427,774 B1 * | 8/2016 | Sheesley | B27K 5/003 |
| 9,591,815 B2 * | 3/2017 | Fujiyama | A01G 9/00 |

(Continued)

FOREIGN PATENT DOCUMENTS

| | | |
|---|---|---|
| KR | 200380226 Y1 | 3/2005 |
| WO | WO-2005011755 A2 | 2/2005 |
| WO | WO-2014/039076 A1 | 3/2014 |

*Primary Examiner* — Regina M Yoo
(74) *Attorney, Agent, or Firm* — Howard & Howard Attorneys PLLC

(57) ABSTRACT

A disinfecting unit and method of operating the same includes a cabinet having a vertical axis, a first lamp coupled to the cabinet directing light in a generally radial direction relative to the vertical axis, a second lamp coupled to the cabinet directing light in at least a partially axial direction relative to the vertical axis and a nebulizer that dispenses disinfecting fluid therethrough.

14 Claims, 17 Drawing Sheets

(56) References Cited

U.S. PATENT DOCUMENTS

| | | |
|---|---|---|
| 9,750,832 B2 | 9/2017 | Paver, Jr. |
| 10,729,796 B2 | 8/2020 | Paver, Jr. |
| 2004/0120845 A1 | 6/2004 | Potember |
| 2004/0222306 A1* | 11/2004 | Fajarillo ............... A47F 7/0078 236/44 C |
| 2005/0178058 A1* | 8/2005 | Rudolph ................ A61K 36/00 47/60 |
| 2006/0284109 A1* | 12/2006 | Scheir ..................... A61L 9/20 250/455.11 |
| 2008/0056933 A1 | 3/2008 | Moore et al. |
| 2008/0206092 A1 | 8/2008 | Crapser et al. |
| 2009/0297399 A1 | 12/2009 | Ryan et al. |
| 2010/0234794 A1 | 9/2010 | Weadock |
| 2011/0243789 A1 | 10/2011 | Roberts |
| 2012/0090236 A1* | 4/2012 | Orr ....................... A01G 31/02 47/62 A |
| 2012/0217415 A1 | 8/2012 | Wormely |
| 2013/0306060 A1 | 11/2013 | Cota |
| 2013/0330235 A1* | 12/2013 | Stibich ..................... A61L 2/24 422/292 |
| 2015/0115170 A1* | 4/2015 | Shostak .................... A61L 2/10 250/492.1 |
| 2015/0118107 A1* | 4/2015 | Sunkara ................... A61L 2/10 250/455.11 |
| 2015/0209457 A1* | 7/2015 | Bonutti .................. C02F 1/325 250/435 |
| 2016/0088868 A1 | 3/2016 | Dobrinsky |
| 2017/0216472 A1 | 8/2017 | Stibich |
| 2017/0312379 A1 | 11/2017 | Stibich |
| 2018/0007845 A1* | 1/2018 | Martin ................... A01G 31/06 |
| 2018/0242539 A1* | 8/2018 | Bhattacharya ........... A01G 9/24 |

* cited by examiner

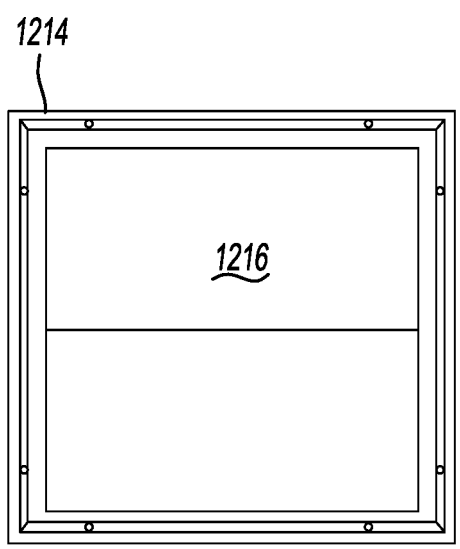
*Fig-13*
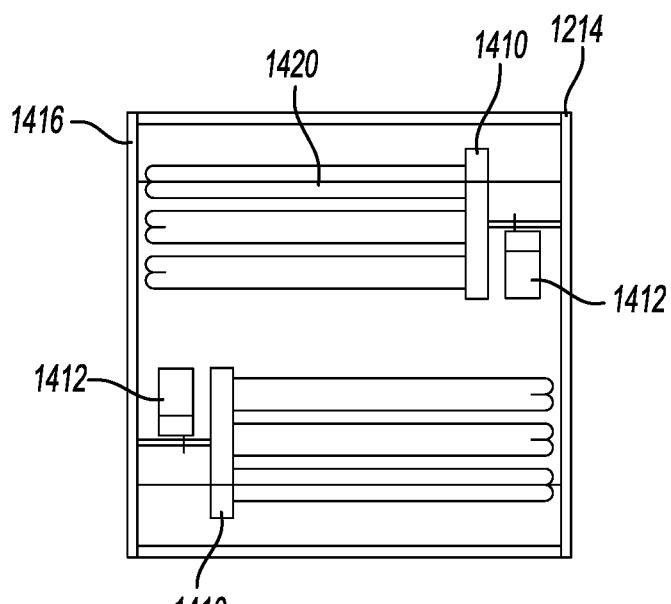
*Fig-14*
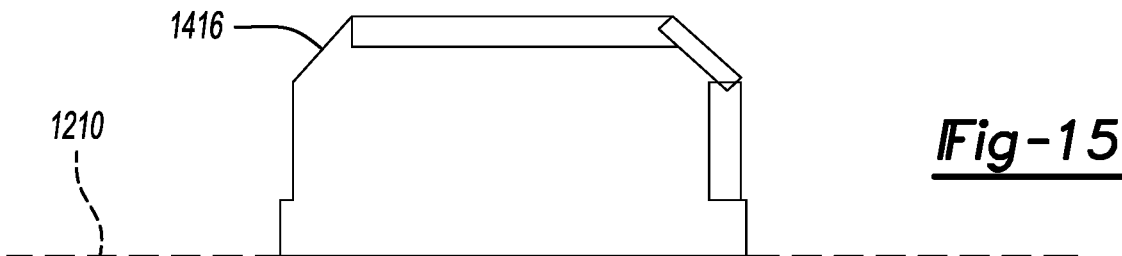
*Fig-15*
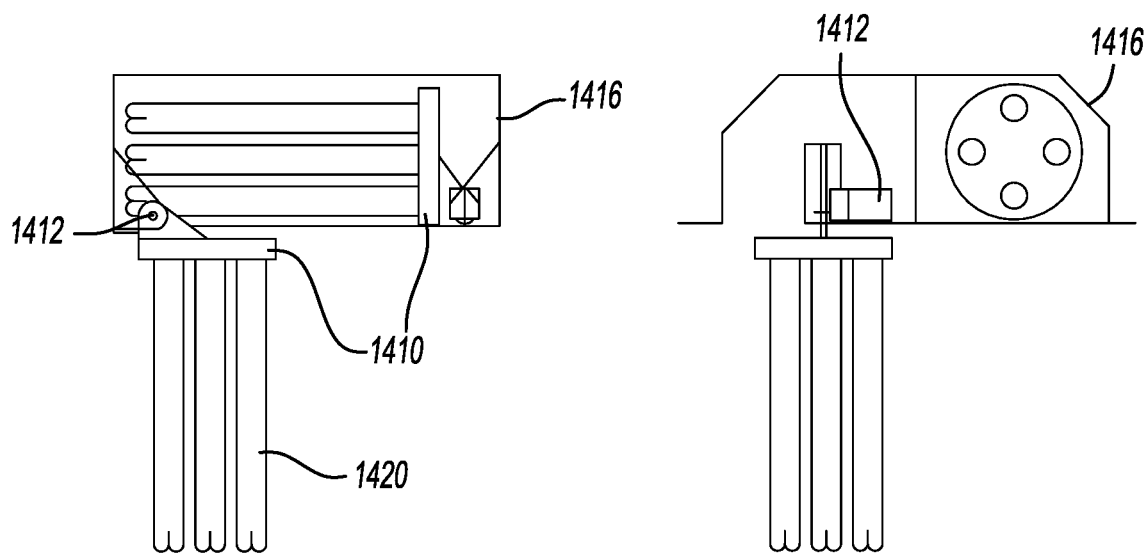
*Fig-16*
*Fig-17*

ULTRAVIOLET AND MISTING DISINFECTING UNIT

CROSS-REFERENCE TO RELATED APPLICATIONS

This application is a divisional of U.S. Ser. No. 15/667,969, filed Aug. 3, 2017, which is a continuation of U.S. Ser. No. 15/003,456 filed on Jan. 21, 2016 (now U.S. Pat. No. 9,750,832), which claims the benefit of U.S. Ser. No. 62/164,775 filed on May 21, 2015 and U.S. Ser. No. 62/107,706 filed on Jan. 26, 2015. The entire disclosures of the above applications are incorporated herein by reference.

FIELD

The present disclosure relates generally to disinfecting units, and more specifically, to a method and disinfecting system for disinfecting a room such as an operating room.

BACKGROUND

This section provides background information related to the present disclosure which is not necessarily prior art.

Each year in the United States, tens of millions of operations are performed. Surgical-site infections result in thousands of deaths each year. In addition to deaths, infections increase the length of stay, add to costs, and triggers lawsuits. Therefore, effectively disinfecting surgical sites, patient rooms and other areas requiring disinfection to reduce infections in every way possible is important.

A surgical site, in particular, contains many pieces of equipment, as well as the physical room itself. Various instruments and devices that are brought into the surgical-site are typically disinfected prior to entry. However, disinfecting the components within the room, and the structure of the room, such as the ceilings, walls, and floors must also be performed on a regular basis. Performing disinfection is a time consuming and labor-intensive process. The disinfection process reduces the time that the operating room is available for surgeries. These factors reduce the overall use, and thus reduce the revenue from the operating space.

It would therefore be desirable to provide a system that allows thorough disinfecting of a room that is not labor intensive.

SUMMARY

This section provides a general summary of the disclosure, and is not a comprehensive disclosure of its full scope or all of its features.

The present disclosure provides a system that combines a nebulizer and light disinfecting in a single easy to deploy unit that operates autonomously once deployed.

In one aspect of the disclosure, a disinfecting unit includes a cabinet having a vertical axis, a first lamp coupled to the cabinet directing light in a generally radial direction relative to the vertical axis, a second lamp coupled to the cabinet directing light in at least a partially axial direction relative to the vertical axis and a nebulizer that dispenses disinfecting fluid therethrough.

In another aspect of the disclosure, a method includes generating a fog through a nebulizer of the disinfecting unit, activating a first lamp to direct light in a generally radial direction relative to the vertical axis and activating a second lamp directing light in at least a partially axial direction relative to the vertical axis.

In yet another aspect of the disclosure, a method of disinfecting a room includes generating a fog through a nebulizer, directing disinfecting light toward a ceiling of the room, and directing disinfecting light toward walls of the room.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected examples and not all possible implementations, and are not intended to limit the scope of the present disclosure.

FIG. 13 is a plan view of a ceiling mounted disinfecting unit.

FIG. 14 is a cutaway view of the disinfecting unit illustrated in FIG. 13 with the doors removed to expose the disinfecting lamps therein.

FIG. 15 is a side view of a disinfecting unit shown relative to a ceiling.

FIG. 16 is a side view of disinfecting lamps extending from a ceiling mounted disinfecting unit housing.

FIG. 17 is a side view of a ceiling mounted disinfecting unit.

Corresponding reference numerals indicate corresponding parts throughout the several views of the drawings.

DETAILED DESCRIPTION

Figure 1A:
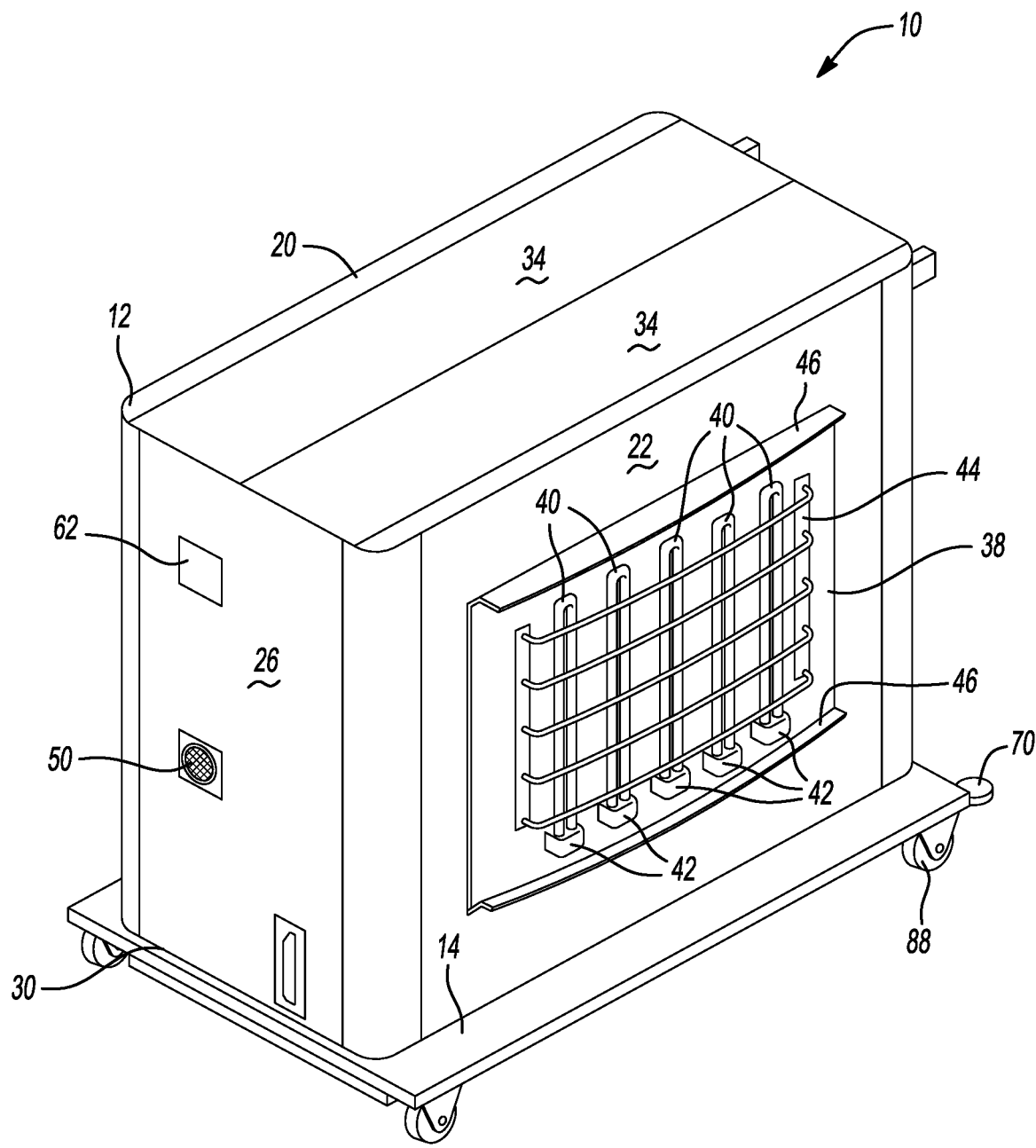
FIG. 1A is a perspective view of a disinfecting unit.

Example examples will now be described more fully with reference to the accompanying drawings.

In the following figures, the same reference numerals will be used to identify the same components. The drawings are to scale, and the geometric relationships (e.g., angles, proportions) between elements shown in the drawings are in accordance with the principles in the present disclosure. However, the drawings are provided for illustrative purposes only and should not be limiting unless set forth in the claims of the present disclosure. Further, the examples set forth herein illustrate various alternative features. The various features, however, may be interchanged in the different examples.

Figure 1B:
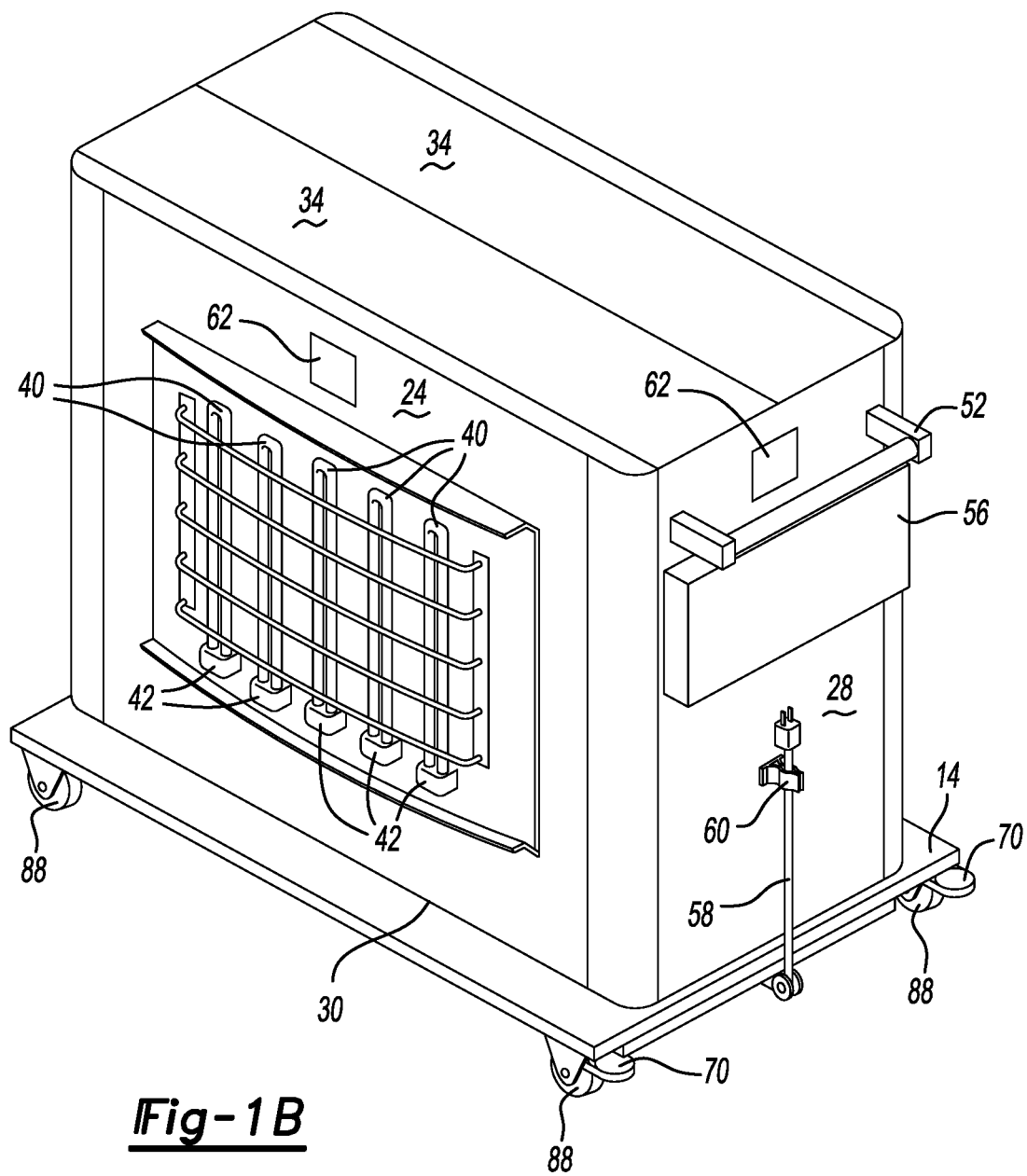
FIG. 1B is a perspective view of the disinfecting unit from the opposite direction of that shown in FIG. 1A.

Referring now to FIGS. 1A and 1B, a disinfecting unit 10 is illustrated, having a cabinet 12 and a base 14. The cabinet 12 is rotatably coupled to the base 14, as will be further described below. The cabinet 12 comprises a top side 20, a first longitudinal side 22, a second longitudinal side 24, a first lateral side 26, and a second lateral side 28. A bottom side 30 also is used to enclose the cabinet 12. The cabinet 12 is used to enclose various components therein for portability. The top side 20 has one or more top side doors 34. In this example, two top side doors are illustrated. The top side doors 34 pivot or rotate so that internal components may extend therefrom, as will be described in more detail below.

The first longitudinal side 22 includes a panel 38 that is used to hold a plurality of disinfecting lamps 40 and their associated sockets 42. The panel 38 may be hinged to provide access to the interior of the cabinet 12 for servicing, adjustments, and the like. The panel 38 may also include a protection grill 44, used to protect the lamps 40 from being contacted. Guards 46 may extend from the first longitudinal side 22 to also help protect the lamps 40 from being contacted.

As shown best in FIG. 1B, the second longitudinal side 24 may also be configured in the same way as the first longitudinal side 22 including a panel 38, lamps 40 and guards 46.

The first lateral side 26 may include a nebulizer 50. The nebulizer 50 is fluidically coupled to a fogger that may include a fluid reservoir and/or pump disposed within the cabinet 12. In this example, the nebulizer 50 may generate a fog or mist of hydrogen peroxide. Of course, depending upon the desired type and amount of disinfecting other nebulized chemicals may be used.

The second lateral side 28 includes a handle 52. A user interface 56 may also be included thereon. The user interface 56 may include a touch screen or a plurality of buttons for activating the disinfecting unit. The user interface 56 may also be detachable and so that the controller of the disinfecting unit 10 may be controlled remotely wirelessly.

A power cord 58 is also shown extending from the unit. A cord retainer 60 may be disposed on the second lateral side 28 for retaining the power cord 58. The power cord 58 may extend into the cabinet 12 for powering the various components disposed therein.

A person sensor 62 may be incorporated on one or more of the longitudinal sides 22, 24 and/or the lateral sides 26, 28. The person sensor 62 may be a combination of one or more different types of sensors, such as an infrared sensor, a motion sensor, a radar sensor, or the like. The person sensor 62 is used for detecting the presence of a person within the room or area to be disinfected. For example, the process may not be allowed to begin the nebulizing portion if a person is detected in the vicinity. Likewise, should a person enter the vicinity during the process, the system may terminate disinfecting using the lamps, or disinfecting using the nebulizer. It may be effective to use only one person sensor 62 because the cabinet 12 rotates relative to the base 14 during the disinfecting process.

The base 14 may have a platform 66 with wheels 68 mounted thereto. The wheels 68 may include locks 70 for preventing the wheels from rolling during the disinfecting process.

Figure 2:
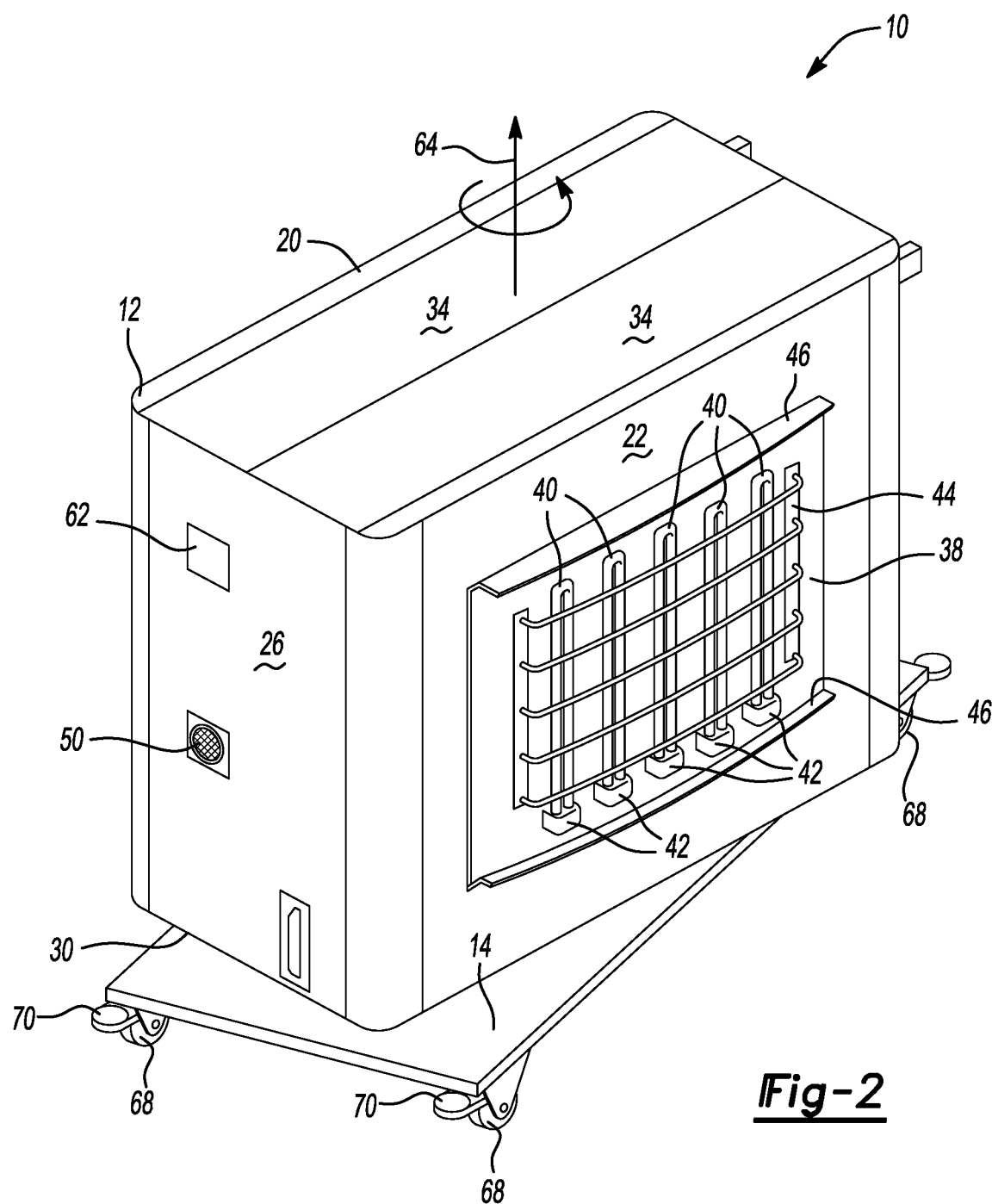
FIG. 2 is a perspective view of a disinfecting unit in a partially rotated position.

Referring now to FIG. 2, the disinfecting unit 10 has a vertical axis 64. The cabinet 12, as mentioned above, rotates relative to the base 14. The cabinet 12 rotates about the vertical axis 64. This allows disinfecting light from the disinfecting lamps 40 to illuminate various surfaces around the disinfecting unit and the nebulizer generated fog to spread in different directions throughout the room.

Figure 3:
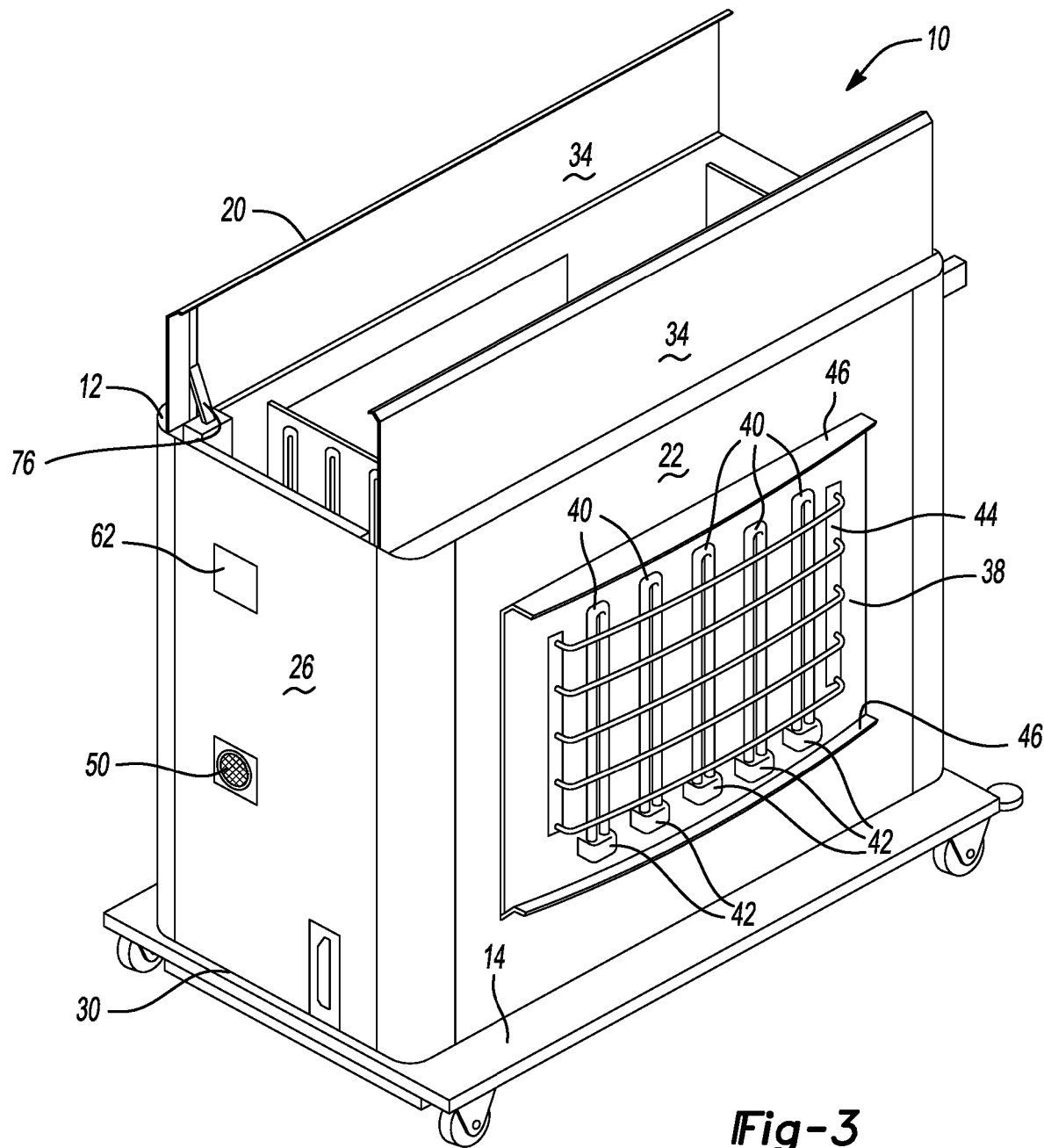
FIG. 3 is a perspective view of a disinfecting unit having top surface doors in an open position.

Referring now to FIG. 3, the top side doors 34 are illustrated in an open position. An actuator 76 is used to open and close the doors 34. The disinfecting unit 10 is an automated unit, and thus, the actuators 76 actuate the doors 34 under control of a controller (illustrated below) when performing the disinfecting process.

Referring now to FIGS. 4A-4D, the disinfecting unit 10 also includes a lamp extension assembly 100. The top side doors 34 are open and the lamp extension assembly 100 extends therefrom. The lamp extension assembly 100 includes a support arm 102. The support arm 102 telescopes from the interior of the cabinet 12. The support arm 102 is fixed to the bottom side 30 of the cabinet 12. Thus, the support arm 102 is fixed relative to the cabinet 12, but the cabinet 12 rotates relative to the base 14. Therefore, the support arm 102 rotates with the cabinet 12 and relative to the room. In this example, the support arm 102 extends vertically from the interior of the cabinet 12 when the top side doors 34 are open.

The support arm 102 is coupled to at least one lamp arm 104. In this example, two lamp arms 104 are set forth. The lamp arms 104 are coupled to a plurality of disinfecting lamps 106. In this example, a lamp support 108 is located at the end of each lamp arm 104. Thus, the lamp arm 104 extends between the lamp support 108 and the support arm 102.

Figure 4A:
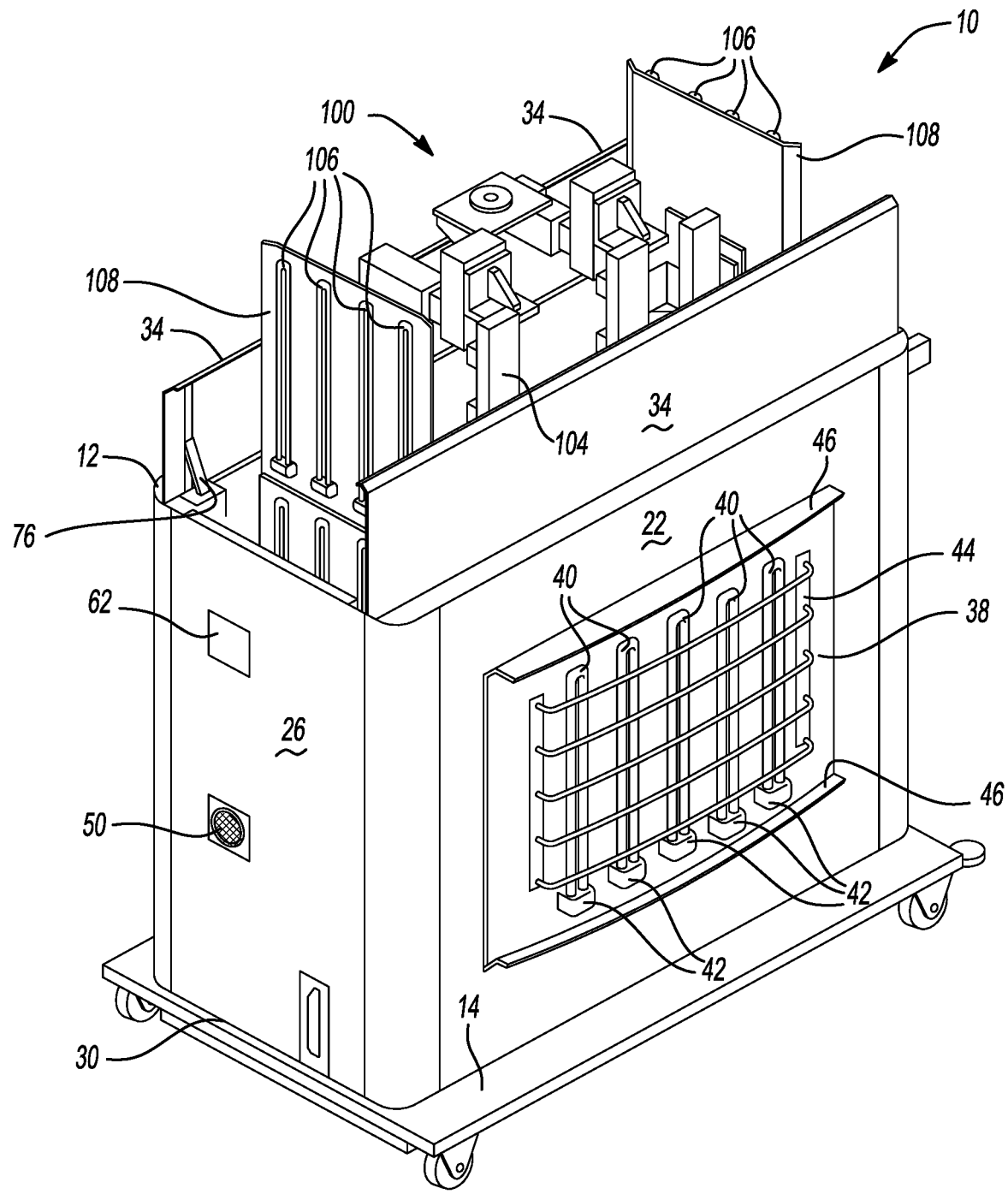
FIG. 4A is a perspective view of a disinfecting unit having a partially extended support arm.

Referring specifically to FIG. 4A, the lamp arms 104 and the lamp support 108 are in a folded position for storage. In FIG. 4A, only the support arm 102 is in a partially extended position.

Figure 4B:
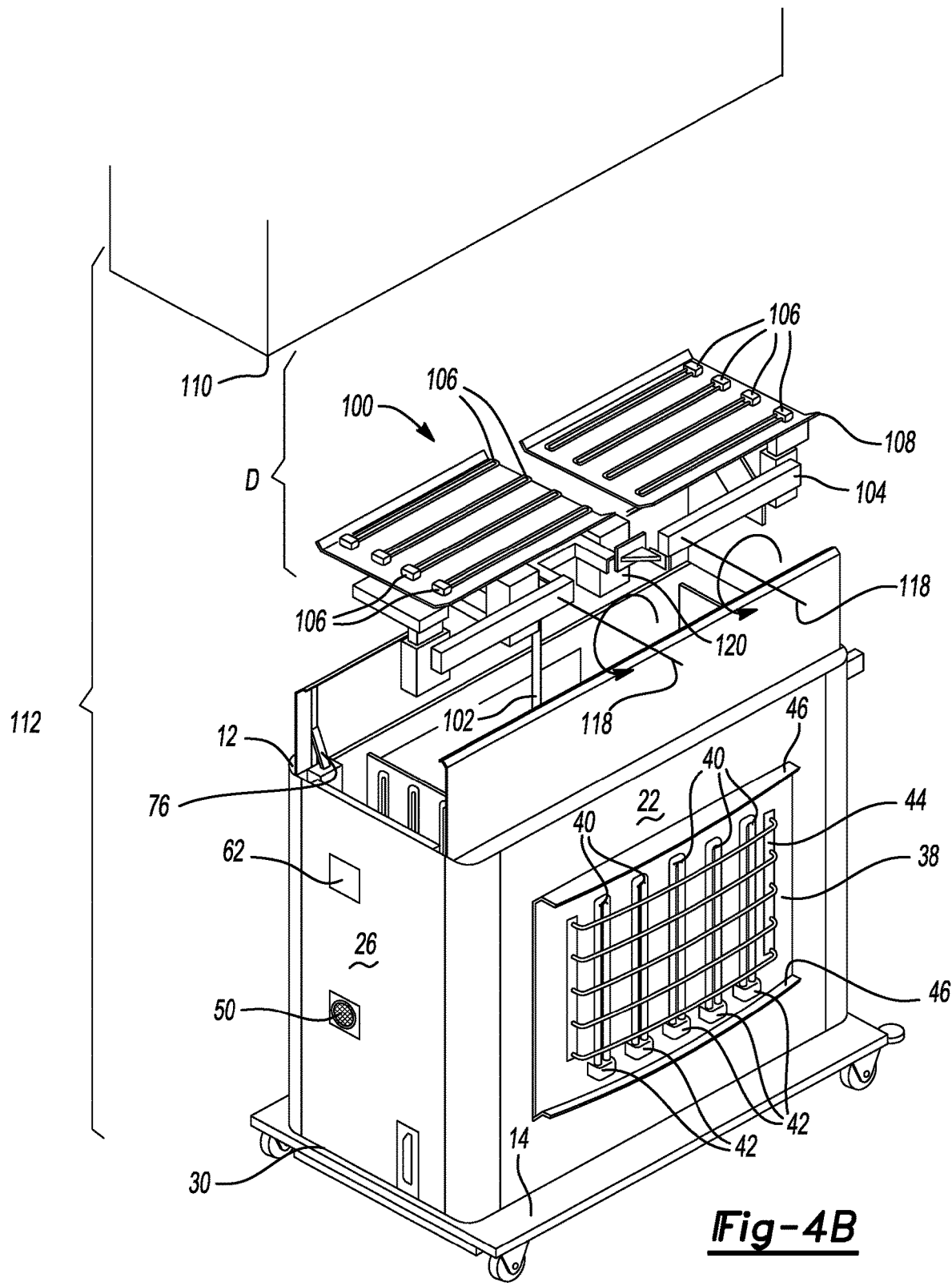
FIG. 4B is a perspective view of a disinfecting unit having a support arm in a fully extended position and lamp arms in an open position. An entire system relative to a ceiling is also illustrated.

Referring specifically to FIG. 4B, the support arm 102 is illustrated in a fully extended position. The length of the extension may vary, depending upon the specific circumstances for the disinfecting unit 10. The disinfecting unit 10 that is used in a very high ceiling environment may include a support arm 102 that extends greater than a disinfecting unit 10 that is within a lower ceiling environment. However, one unit that has a programmable height may be used. A ceiling 110 is illustrated adjacent to the disinfecting unit 10 to form a disinfecting system 112. The ceiling 110 may be a non-porous material that does not allow germs or other microbes to hide therein. The ceiling 110 may be a suspended ceiling. The lamp arm 104 may rotate about an axis 118 using a motor 120. In this example, the lamp arms 104 rotate in opposite directions relative to their respective axes 118.

Figure 4C:
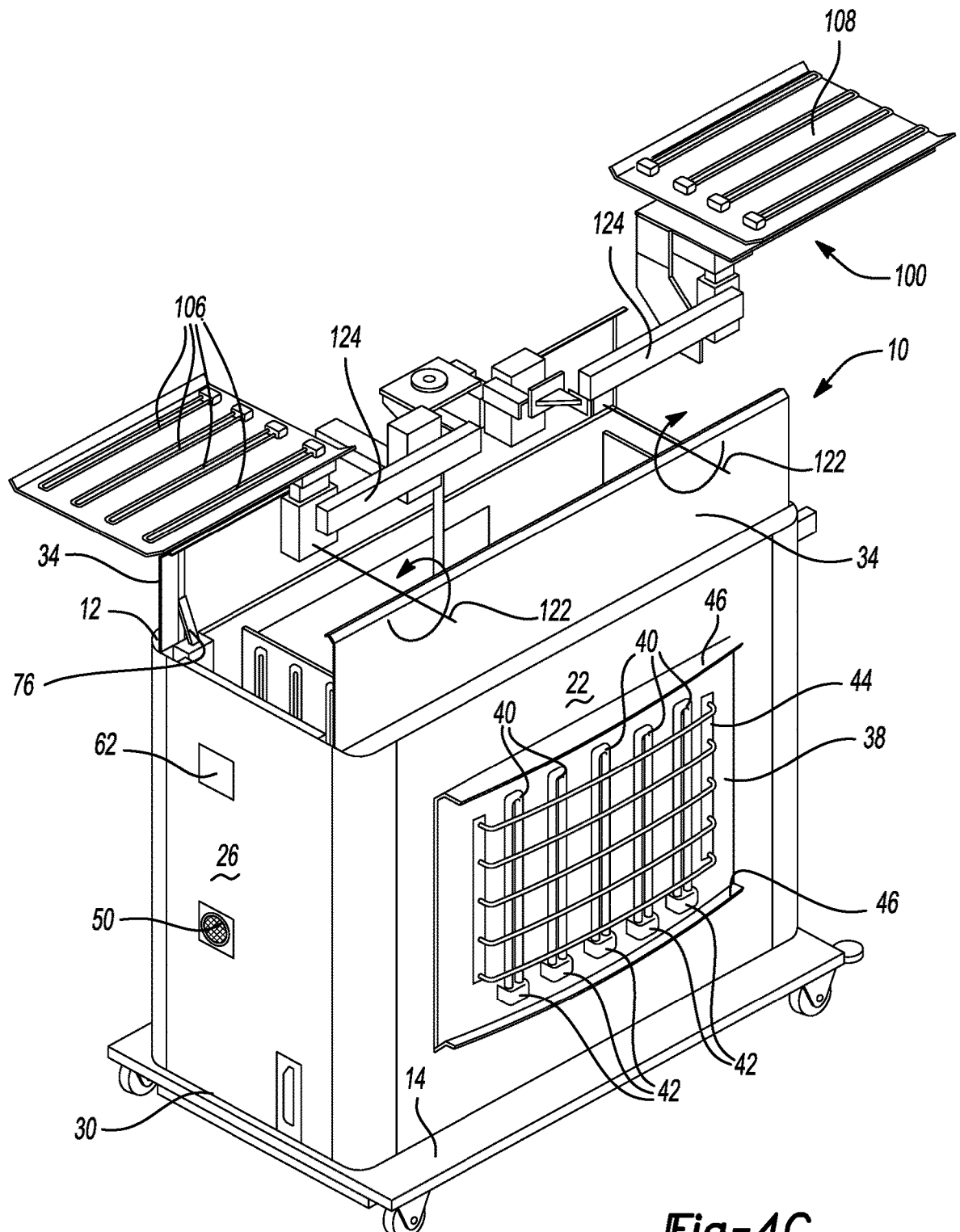
FIG. 4C is a perspective view of a disinfecting unit having the lamp arms and lamp supports in a fully extended position.

Referring now specifically to FIG. 4C, the lamp support 108 rotates about an axis 122 through the use of a motor 124. Each lamp arm 104 may be coupled to the lamp support 108 using the motor 124. The motor 124 rotates the lamp support 108 about the axis 122. The amount that the motor 124 may rotate the lamp support 108 may vary, depending upon the desired conditions. Therefore, the lamp support position may be programmable. Each lamp support 108 may be at a different angle relative to the disinfecting unit 10. Depending upon the conditions, this may provide an advantage to obtain light directed at various surfaces at different angles. Also, the angle of the lamp support 102 relative to the disinfecting unit 10 may vary during the process. That is, one or more lamp supports 108 may be provided at different angles for different time periods during the disinfecting process.

Figure 4D:
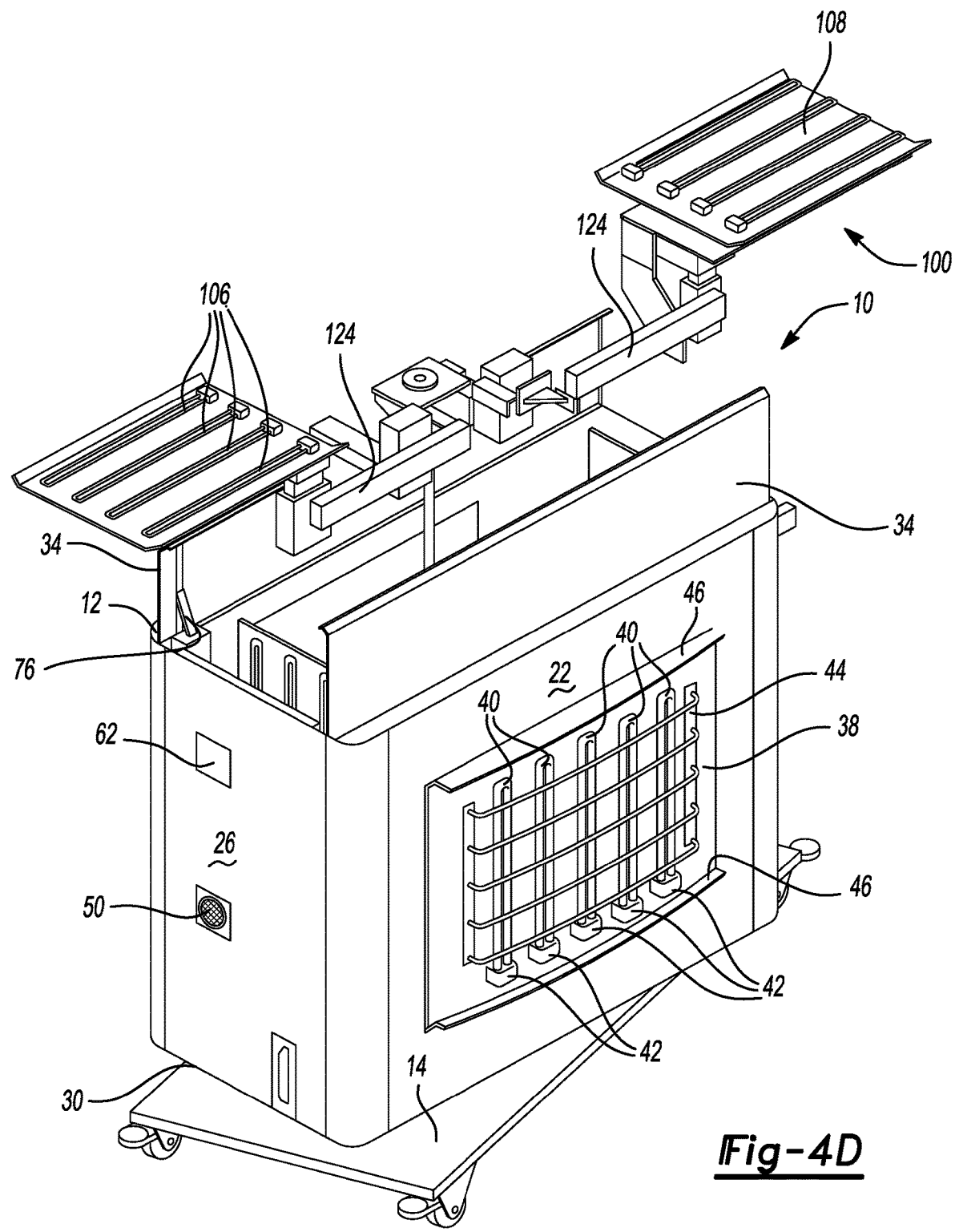
FIG. 4D is a perspective view of a disinfecting unit in a partially rotated position having the support arm and lamp arms in a fully extended position.

Referring now to FIG. 4D, the cabinet 12 is illustrated with the lamp support 108 extended, and the support arm 102 extended. In this manner, the lamps 106 and the lamps 40 are energized to provide disinfecting around a particular room or enclosure.

Figure 5:
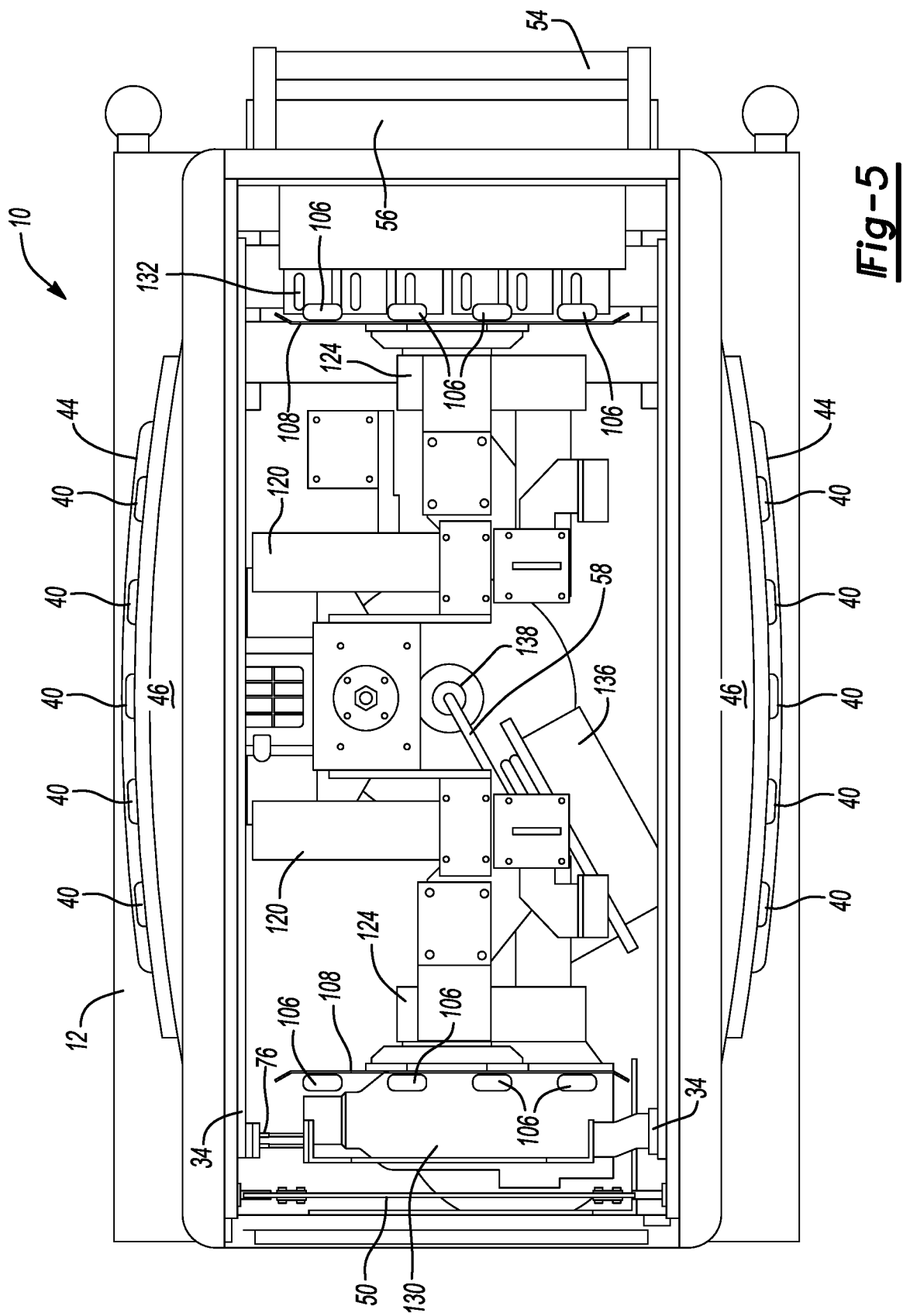
FIG. 5 is a top view of a disinfecting unit having the top surface doors in an open position.

Referring now to FIG. 5, a top view of the disinfecting unit 10 is illustrated with the top side doors 34 in an open position. In this example, a disinfectant or fogger tank 130 is illustrated coupled to the nebulizer 50. The fogger tank 130 may include a pump communicating disinfecting fluid to the nebulizer 50. A controller 132 is used to control the various functions, including the motors for moving the support arm 102, the lamp arm 104, and the lamp support 108. The controller 132 may also be used to control the fogger 130. The controller 132 may also be coupled to the user interface 56.

The power cord 58 is illustrated entering the internal portions of the cabinet 12 through an opening 138. The power cord 58 is coupled to a power distribution unit 134. Each of the electrical components within the disinfecting unit 10 may be electrically coupled to the power distribution unit 134.

The disinfecting unit 10 also includes a motor 136 that is used to rotate the cabinet 12 relative to the base 14. The opening 138 is the position that corresponds to the vertical axis 64 of FIG. 2 about which the cabinet 12 rotates.

Figure 6:
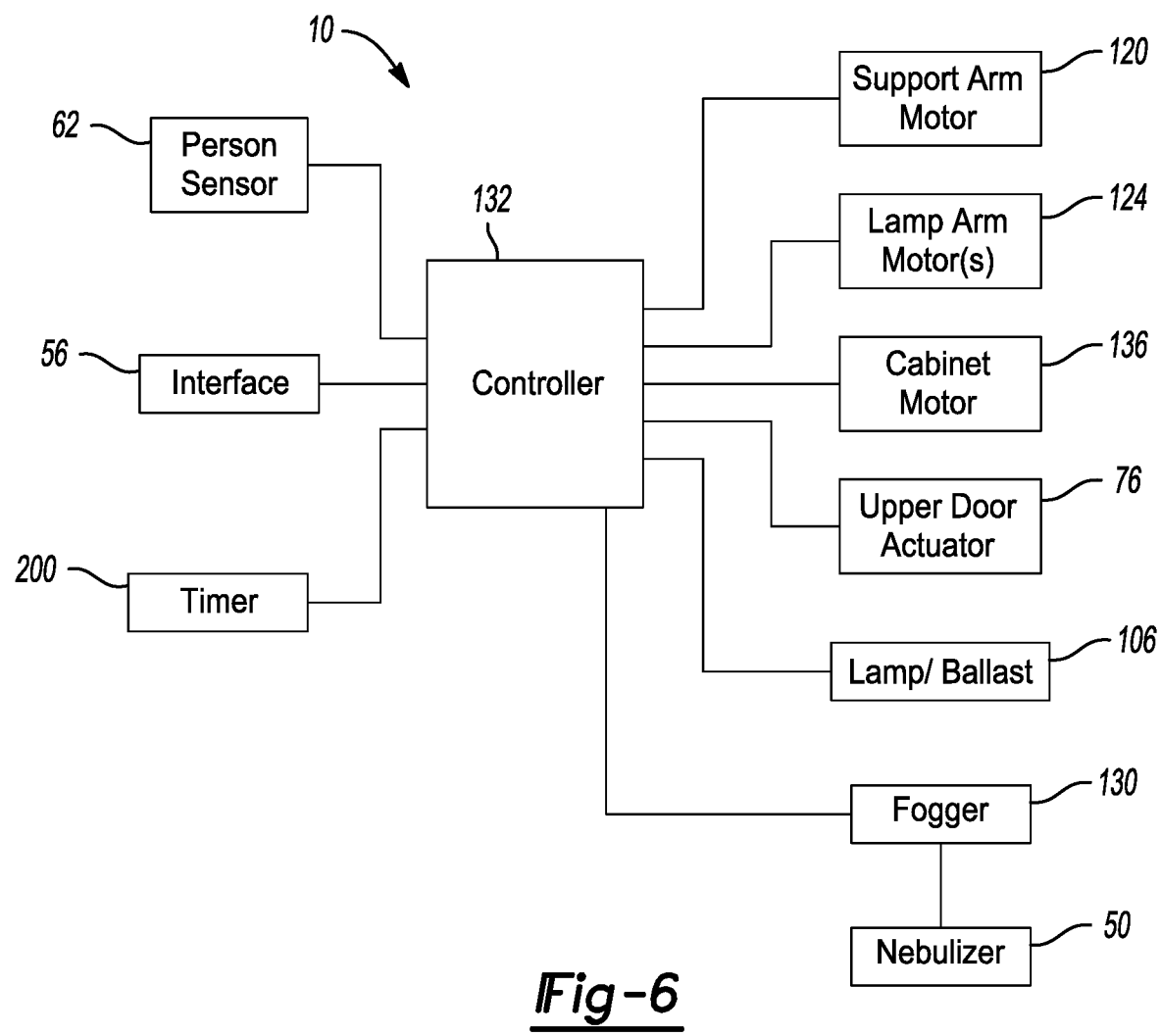
FIG. 6 is a simplified block diagrammatic view of the disinfecting unit.

Referring now to FIG. 6, a simplified block diagrammatic view of the disinfecting unit 10 is illustrated. In this example, the controller 132 is coupled to the person sensor 62, a user interface 56, and a timer 200. The timer 200 is used for timing various time periods for events occurring during the disinfecting process. The timer 200 is illustrated as a separate item, but may be included as part of the controller 132.

The controller 132 is used to control various elements of the disinfecting unit 10, including the support arm motor 120, the lamp arm motor or motors 124, a cabinet motor 136, the upper door actuator 76, the lamps and lamp ballasts 106, and the fogger 130 and the pump therein.

The controller 132 may be microprocessor based and may include internal memory for storing commands to be executed thereby. The controller 132 may be programmed using the user interface 56. The controller 132 may be preprogrammed with one or more disinfecting cycles for a variety of conditions.

Figure 7:
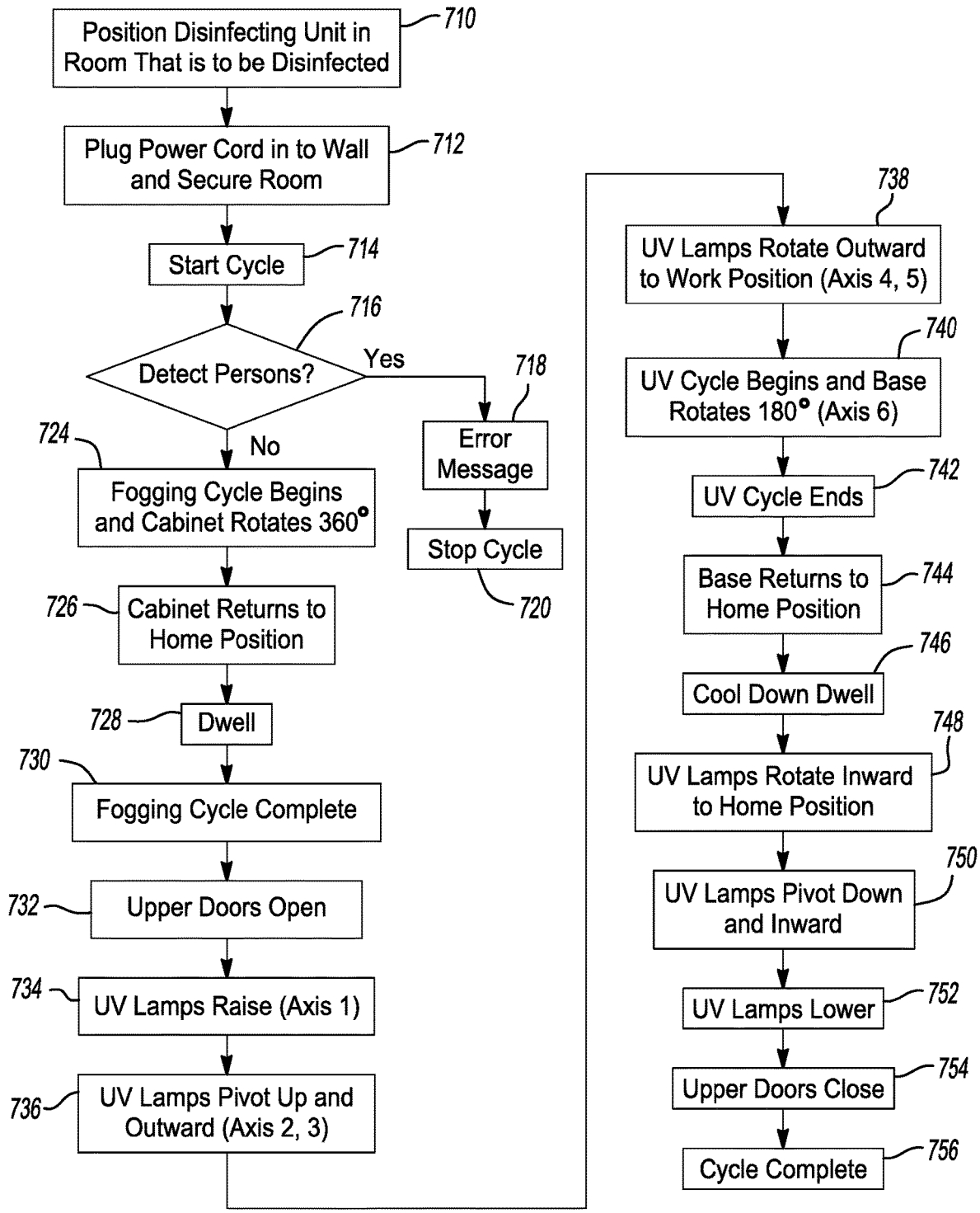
FIG. 7 is a flow chart of a method for operating the disinfecting unit.

Referring now to FIG. 7, a method for performing disinfecting using the disinfecting unit 10 illustrated in FIGS. 1-6 is set forth. In steps 710, the disinfecting unit is positioned within the room to be disinfected. In this example, various operating conditions are controlled so as the current draw is less than 20 amps. In step 712, the power cord is plugged to a wall and the room is secured. In step 714, a start cycle is initiated at the disinfecting unit 10. The start cycle may be initiated at a predetermined time after triggering using the user interface 56. That is, a person may trigger the unit to start, but the start time is delayed to allow the person to leave the room to be disinfected. In step 716, the detection of persons within the area is detected by the person sensors. When persons are detected, an error message 718 may be generated. The error message may be accompanied by a buzzer, bell, or other audible tone or visual indicator such as a strobe light. In step 720, the disinfecting process is stopped. The detection of persons may be performed continuously during the execution of the various other steps set forth below. That is, at any time, the process may be stopped upon the detection of a person in the vicinity of the disinfecting unit 10.

When persons are not detected, the fogging cycle begins, and the cabinet 12 rotates at step 724. The fogging cycle may take place for various amounts of time, such as 20 seconds. The amount of time may depend on various factors including, but not limited to, the amount of fixtures within the room, the room geometry, and the disinfecting chemicals. In step 726, the cabinet 12 returns to the home position (like FIG. 1A and FIG. 1B), and in step 728 the cabinet 12 remains at the home position for a dwell time. In step 730, the fogging cycle is complete.

In step 732, the upper doors 34 illustrated in FIG. 1 are opened. As mentioned above, the detection of persons may be performed continually. In step 734, the UV lamps are raised by the vertical axis and through the use of the support arm 102. In step 736, the UV lamps pivot up and outwards, using the motor 120. In step 738, the UV lamps and supports rotate outwards using the motor 124 to a working position. As briefly mentioned above, the working position of the lamp and lamp base may vary depending upon the desired results and various geometries within the room. These positions may be programmed into the controller. In step 740, the UV cycle begins, and the cabinet 12 rotates relative to the base 14. The UV lamps, including the lamps and lamp support, and the lamps on the longitudinal side panels 38, are activated. In step 742, the UV cycle ends.

In step 744, the cabinet 12 returns to the home position. In step 746, the cool down of the unit in a dwell position is performed. This allows time for the ultraviolet lamps to cool down before storage. In step 748, the UV lamps rotate inwards to the home position. In step 750 the UV lamps pivot down and inwards. In step 752, the UV lamps lower. In step 754 the upper doors close. In step 756 the cycle is complete. It should be noted that various durations of time periods may be associated with each of the steps, and may vary depending upon various factors in the environment in which disinfecting is taking place.

Figure 8:
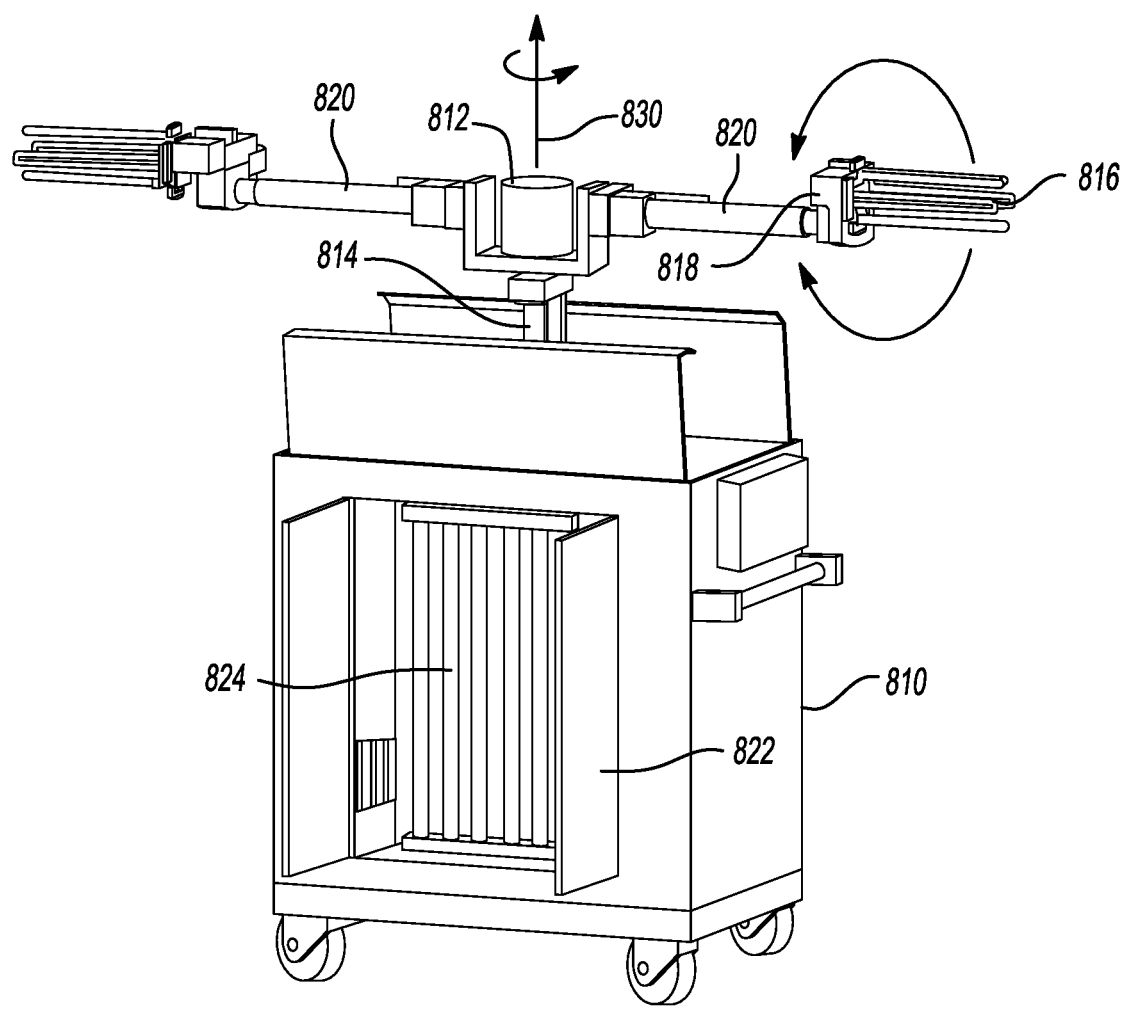
FIG. 8 is a perspective view of an alternate example of a disinfecting unit having a nebulizer coupled directly to a support arm 102 and having longitudinal side doors covering the longitudinal side lamps.

Referring now to FIG. 8, one alternative example of a disinfecting unit 810 is set forth. In this example, a nebulizer 812 is located on or coupled to a support arm 814. The ultraviolet lamps 816 are also configured without a lamp support, as in the previous example. In this example, a lamp receptacle 818 may pivot relative to a lamp arm 820.

Lateral side doors 822 may be used to protect the lateral side lamps 824. Lateral side lamps 824 may be located on each lateral side of the disinfecting unit 810.

The operation of the disinfecting unit 810 is similar, except that the lateral side doors 822 are opened prior to the lateral side lamps 824 being activated for disinfecting of a room. The main difference between the method set forth in FIG. 7 and that which would be used for the disinfecting unit 810 of FIG. 8, is that the support arm 814 would be extended prior to fogging of the area.

The lamp arms 820 rotate around a vertical axis 830 during operation. The arms 820 extend out of the disinfecting unit 810 in the direction of the axis 830 (vertically) when in use.

Figure 9A:
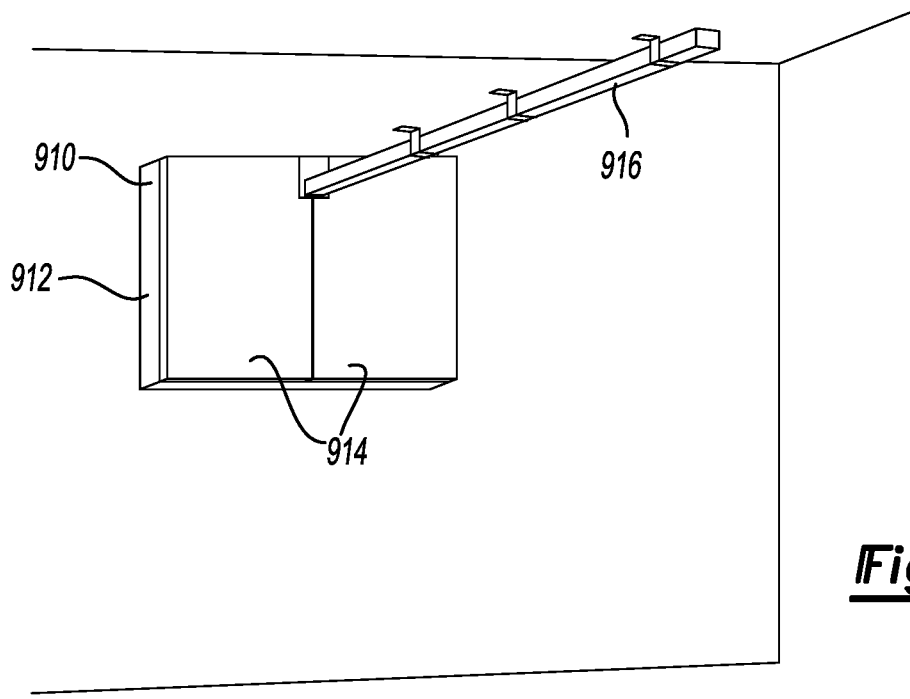
FIG. 9A is a perspective view of a wall mounted disinfecting unit in a closed position.
Figure 9B:
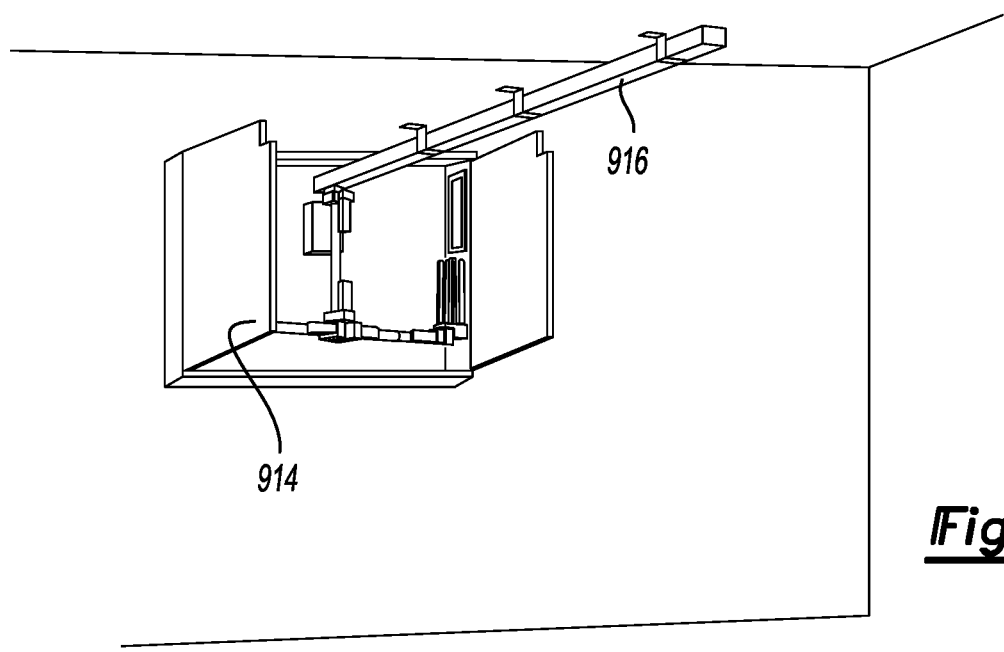
FIG. 9B is a perspective view of a disinfecting unit having open doors prior to deployment.
Figure 9C:
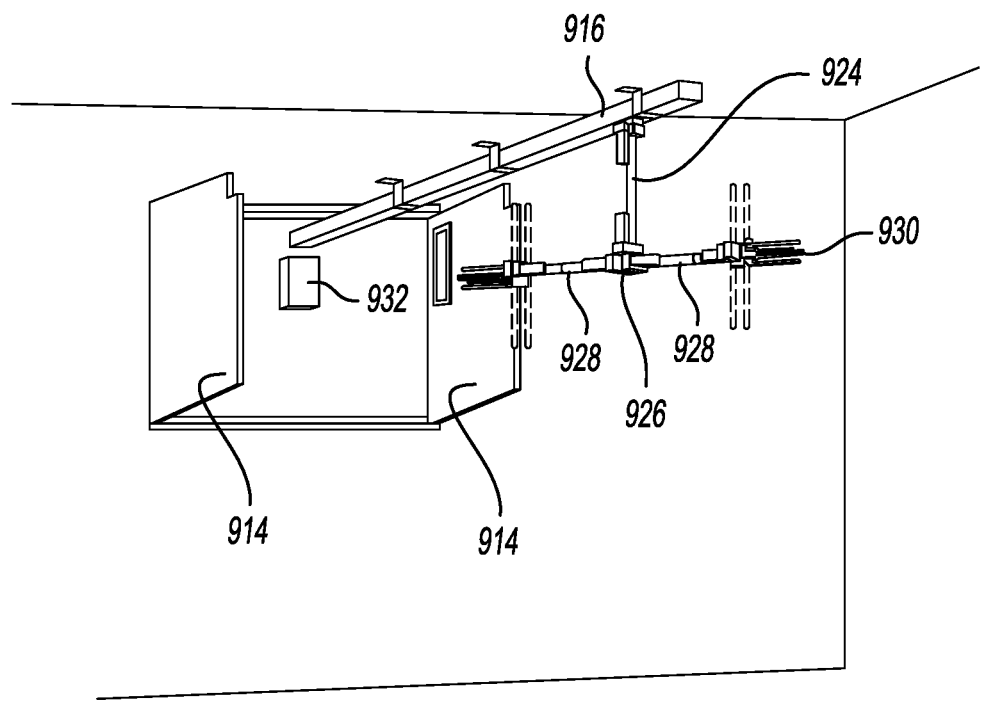
FIG. 9C is a perspective view of a fully deployed support arm relative to a disinfecting cabinet.

Referring now to FIGS. 9A-9C, a wall mounted disinfecting unit 910 is illustrated. In this example, a wall cabinet 912 has doors 914 that open. A track 916 extends from the cabinet 912. The track 916 may be located on, or suspended from, a ceiling of the room. FIG. 9B shows a support arm 924 that houses a nebulizer 926 and has lamp arms 928 that also extend therefrom.

In FIG. 9B, the doors 914 are opened prior to the support arm 924 moving the lamp arms 928, the nebulizer 926, and the disinfecting lamps 930, therefrom. The track 916 may also conceal a chain or belt mechanism for moving the support arm 924 relative to the track 916. Of course, a motor mounted to the support arm may be used to move the support arm.

The lamp arms 928 are used to support disinfecting lamps 930. One set of disinfecting lamps extend from each lamp arm 928. In this example, the disinfecting lamps 930 may pivot relative to the lamp arms 928 and the support arm 924 may rotate around its axis to position the lamp arms 928 at a desired area of the room. A heater and tank 932 are used to provide the disinfecting fluid through conduits (not shown) in the track and the support 924 to provide the nebulizer 926 with disinfecting fluid.

Figure 10:
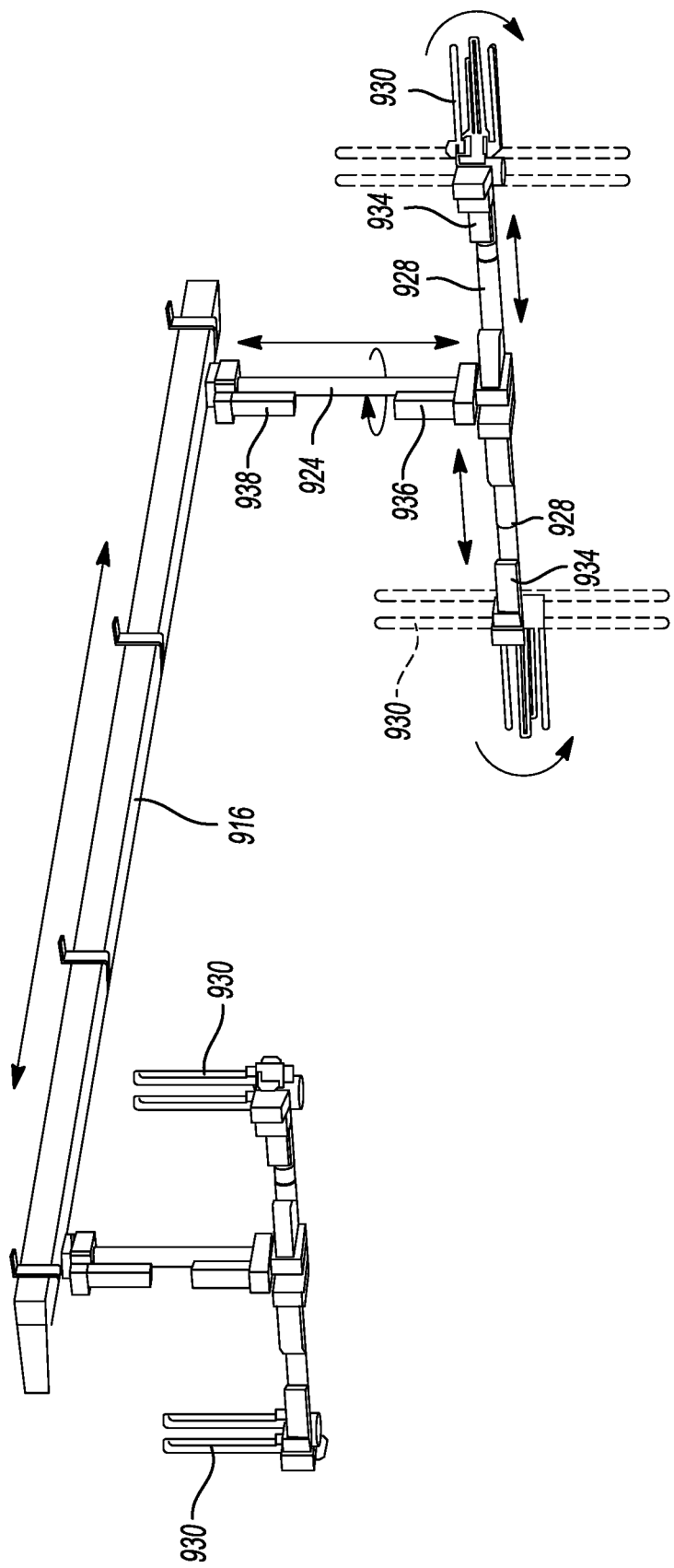
FIG. 10 is a detailed view of a track and support arm in an at-rest and in a fully-deployed position.

Referring now to FIG. 10, details of the track 916, support arm 924, lamp arms 928, and the disinfecting lamps 930 are illustrated. The left-most portion of FIG. 10 illustrates the internal structure of the disinfecting unit in an at-rest and in-cabinet position. The cabinet was removed to enhance clarity. At the right-most portion of FIG. 10, the support arm 924 is telescopically extended in a vertical direction. The lamp arms 928 are also telescopically extended, but in a horizontal direction. The disinfecting lamps 930 are also rotated relative to the lamp arms 928 into a disinfecting position.

A plurality of motors 934 may be used to rotate the disinfecting lamps 930 into a desired position. As well, a motor 936 coupled to the support arm 924, may be used to rotate the support arm and position the lamp arms 928 to the desired position.

An up/down limiter 938 may be used to move and limit the movement of the support arm 924 in a vertical direction.

Figure 11:
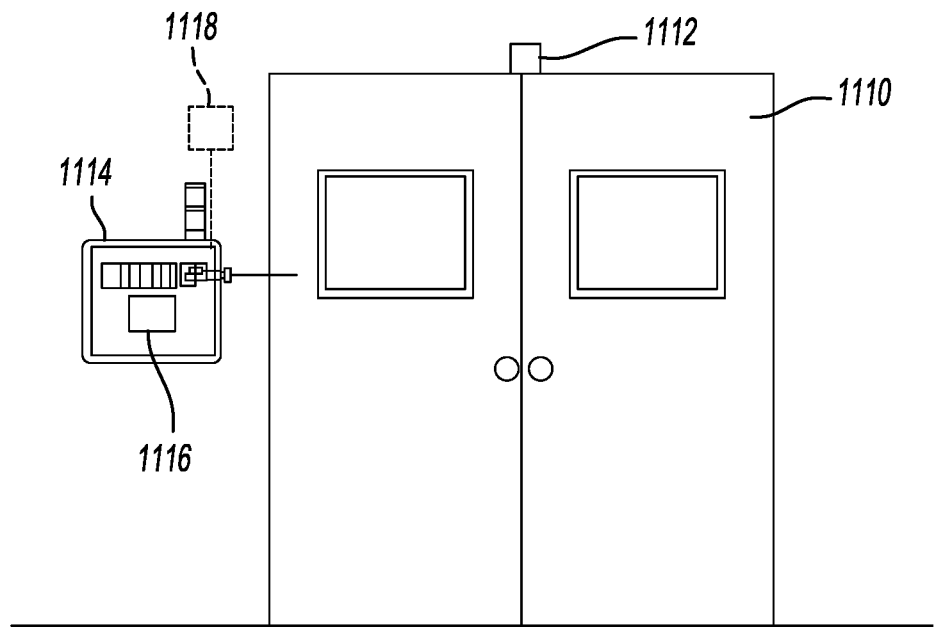
FIG. 11 is an elevational view of a control panel and doors of a room to be disinfected.

Referring now to FIG. 11, an operating room may have doors 1110 with a door locking mechanism 1112. The door locking mechanism 1112 may be controlled by a control panel 1114. Likewise, the control panel 1114 may be used to control the operation of the disinfecting unit 910 illustrated in FIGS. 9 and 10 above. A user interface 1116 may be used to program and activate the system. The user interface 1116 may also be in communication with a people sensor 1118 located within the operating room or other room to be disinfected. In this manner, the system will not start the disinfecting process upon the detection of person by the people sensor 1118 in the operating room.

Figure 12:
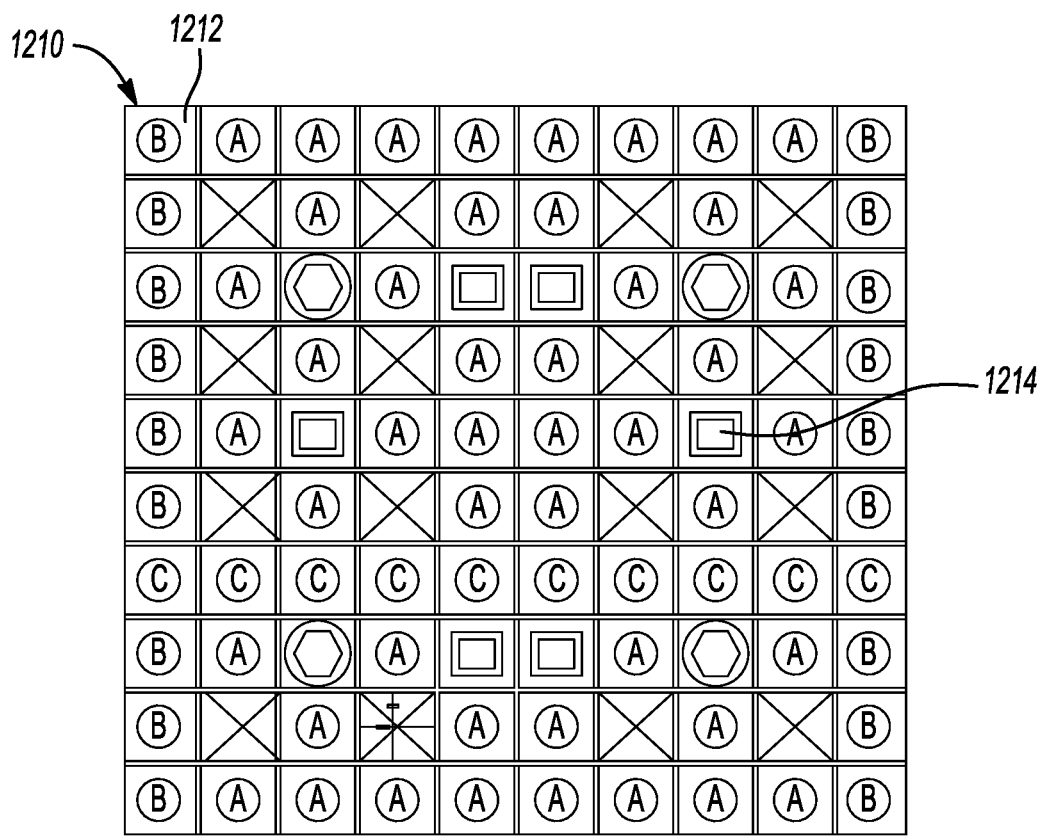
FIG. 12 is a plan view of a ceiling system having disinfecting units mounted thereto.

Referring now to FIG. 12, a ceiling 1210 is illustrated having a plurality of ceiling segments 1212. The ceiling segments 1212 may be formed from antimicrobial panels. The ceiling may comprise a plurality of lights and a plurality of disinfecting units 1214. The disinfecting units 1214 are illustrated in further detail in the following Figures. In FIG. 13, the disinfecting unit has cover doors 1216. In FIG. 14, a plurality of lamp holders 1410 are illustrated. The lamp holders 1410 may be in communication with a motor 1412. The motors 1412 may be used to rotate the lamp holders 1410 relative to the ceiling 1210. That is, the lamp holders 1410 may be rotated out of the housing 1416 so that the lamps 1420 extend below the ceiling 1210. The housing 1416 may be recessed into the ceiling 1210, as illustrated in FIG. 15. In FIG. 16, a lamp holder 1410 is rotated out of the housing 1416 so that the disinfecting lamps 1420 extend in a perpendicular direction to the ceiling. In FIG. 17, one of the lamp holders 1410 is not extended out from the housing 1416. However, in operation, each lamp holder 1410 may extend from the housing beneath the ceiling line 1210.

The foregoing description of the examples has been provided for purposes of illustration and description. It is not intended to be exhaustive or to limit the disclosure. Individual elements or features of a particular example are generally not limited to that particular example, but, where applicable, are interchangeable and can be used in a selected example, even if not specifically shown or described. The same may also be varied in many ways. Such variations are not to be regarded as a departure from the disclosure, and all such modifications are intended to be included within the scope of the disclosure.

What is claimed is:

1. A disinfecting unit comprising:
   a base, a cabinet and a motor coupled in driving relationship to the cabinet, wherein the cabinet defines a vertical axis and is supported on the base for rotation when driven by the motor;
   a first lamp coupled to the cabinet directing light in a generally radial direction relative to the vertical axis;
   a second lamp coupled to the cabinet directing light in at least a partially axial direction relative to the vertical axis; and
   a nebulizer that dispenses disinfecting fluid therethrough.

2. The disinfecting unit of claim 1, wherein the base comprises a plurality of wheels.

3. The disinfecting unit of claim 1 further comprising a support arm coupled to the cabinet, said support arm coupled to the second lamp.

4. The disinfecting unit of claim 3 wherein the support arm comprises a telescopic support arm.

5. The disinfecting unit of claim 1 wherein the first lamp comprises a first plurality of lamps and the second lamp comprises a second plurality of lamps.

6. The disinfecting unit of claim 1 wherein the cabinet has a plurality of sides one of which, a first side comprises the first lamp and a second side comprises a third lamp.

7. The disinfecting unit of claim 1 wherein the cabinet has a pair of longitudinal sides, a first longitudinal side comprising the first lamp and a second longitudinal side comprising a third lamp.

8. The disinfecting unit of claim 1 wherein the nebulizer is coupled to the cabinet.

9. The disinfecting unit of claim 1 wherein the cabinet comprises a plurality of doors in a top side enclosing a support arm coupled to the second lamp.

10. The disinfecting unit of claim 1 further comprising a fourth lamp, said second lamp and the fourth lamp are coupled to a support arm, the second lamp and the fourth lamp are independently aimed.

11. The disinfecting unit of claim 1 further comprising a user interface coupled to the cabinet.

12. The disinfecting unit of claim 1, wherein the first lamp comprises a first ultraviolet lamp and the second lamp comprises a second ultraviolet lamp and the nebulizer acts to nebulize hydrogen peroxide.

13. The disinfecting unit of claim 1 further comprising a pump and a disinfectant tank in fluid communication with the nebulizer.

14. The disinfecting unit of claim 1 wherein the first lamp is coupled to a first side of the cabinet, the second lamp is coupled to a support arm, a third lamp is coupled to a second side of the cabinet and a fourth lamp is coupled to the support arm and is individually positionable relative to the second lamp.

* * * * *